(12) United States Patent
Bowles et al.

(10) Patent No.: US 6,186,994 B1
(45) Date of Patent: Feb. 13, 2001

(54) LAYERED TAMPON

(75) Inventors: Virginia Bowles, Cincinnati, OH (US); Jon Arthur Curtis, Ticonderoga, NY (US); Jenéne Marie Francis, Cincinnati, OH (US)

(73) Assignee: The Procter & Gamble Company, Cincinnati, OH (US)

( * ) Notice: Under 35 U.S.C. 154(b), the term of this patent shall be extended for 0 days.

(21) Appl. No.: 09/126,491

(22) Filed: Jul. 30, 1998

(51) Int. Cl.[7] ........................................ A61F 13/15

(52) U.S. Cl. ................................ 604/385.17; 604/904

(58) Field of Search .......................... 604/372, 367, 604/378, 385.1, 904

(56) References Cited

U.S. PATENT DOCUMENTS

| 3,628,534 | * | 12/1971 | Donohue | 604/904 |
| 3,695,270 | * | 10/1972 | Dostal | 604/904 |
| 4,274,412 | * | 6/1981 | Austin | 604/904 |
| 4,787,895 | * | 11/1988 | Stokes et al. | 604/358 |
| 5,006,116 |   | 4/1991 | Alikhan et al. | |

FOREIGN PATENT DOCUMENTS

WO 98/20825   5/1998  (WO).

* cited by examiner

*Primary Examiner*—Dennis Ruhl
(74) *Attorney, Agent, or Firm*—Matthew P. Fitzpatrick; Kevin C. Johnson; Theodore P. Cummings

(57) ABSTRACT

This invention relates to absorbent tampons. More particularly, the invention relates to an improved absorbent tampon having an improved fluid acquisition rate without decrease in capacity or fluid retention characteristics. This is accomplished by an absorbent tampon comprising a layered structure constructed from layers of rayon and cotton. The tampon pledget of the present invention is in the form of a laminar pad of discrete layers. The pledget comprises at least an uppermost layer, a lowermost layer, and at least one intermediate layer positioned between the uppermost layer and the lowermost layer. The uppermost layer and the lowermost layer are each comprised primarily of rayon. At least one intermediate layer is comprised primarily of cotton. In a particular aspect of the invention, the outer layers (i.e. the uppermost layer and the lowermost layer) are comprised of at least about 60% rayon, more preferably at least about 90% rayon, and even more preferably entirely of rayon. In another aspect of the invention at least one intermediate layer is comprised of at least about 60% cotton, more preferably at least 90% cotton, and even more preferably entirely of cotton.

9 Claims, 6 Drawing Sheets

LAYERED TAMPON

FIELD OF THE INVENTION

This invention relates to absorbent tampons. More particularly, the invention relates to an improved absorbent tampon having an improved fluid acquisition rate without decrease in capacity or fluid retention characteristics. This is accomplished with a tampon comprising layers of differing material composition. The materials are selected for their differing properties with respect to each other such that the resulting tampon combines the advantages of the properties of the various layers.

BACKGROUND OF THE INVENTION

A wide variety of absorbent catamenial tampons have long been known in the art. Most currently commercially available tampons are made from a tampon pledget which has been compressed into a substantially cylindrical form. Tampon pledgets of a variety of types and constructions have been described in the art. Prior to compression, the pledget may be rolled, spirally wound, folded, or assembled as a rectangular pad of absorbent material. Tampons made from a generally rectangular pledget of absorbent material have been popular and successful in the market.

Tampons have been constructed from a variety of absorbent materials. Preferred materials for tampons have included rayon and cotton. These materials are particularly useful in tampon construction because of their low cost, good absorbency, and proven effectiveness in such products. Most current commercially available tampons are made of either rayon, cotton, or homogenous blends of the two. One advantage of rayon is that it typically demonstrates a higher rate of absorbency than cotton. Cotton, on the other hand, is more likely than rayon to retain previously absorbed fluids when subjected to external pressure. Tampons constructed of homogenous blends of cotton and rayon have attempted to combine the advantages of both materials.

Additionally, numerous attempts have been made in the art to provide a tampon pledget with a layered structure. For example U.S. Pat. No. 3,610,243 entitled "Reticulated Paper Tampon" and issued Oct. 5, 1971 to Jones, Sr. discloses a tampon made up of a multiplicity of tissue paper layers which have been folded into a multi-layered tampon. The Jones device, however, does not incorporate layers of different material construction in order to combine the benefits of each.

U.S. Pat. No. 3,051,177 issued to Wilson on Aug. 28, 1962 and U.S. Pat. No. 3,079,921 issued to Brecht et al. on Mar. 5, 1963, disclose a two layer structure and a three layer structure, respectively. The layers of the Wilson device consist of an absorbent layer and a permeable cover to protect the absorbent layers. These layers are folded upon themselves several times to form a six-ply pad. The Brecht device discloses a three layer tampon composed of a resilient layer sandwiched between two absorbent layers. All three layers are folded upward to form the tampon.

U.S. Pat. No. 3,371,666 issued to Lewing on Mar. 5, 1968 and U.S. Pat. No. 3,628,534 issued to Donohue on Dec. 21, 1971, each disclose a generally planar tampon made up of a plurality of layers. Both the Lewing and the Donohue devices, however, incorporate cotton layers on the outside of the pledget with layers of superabsorbent material on the inside. The superabsorbent material is a stand alone film in the Donohue device and is distributed on a carrier web in the Lewing device.

While many of the above-described devices and other tampons currently available have been successful and have gained acceptance in the marketplace, the search for an improved absorbent tampon has continued. Each of the above-described devices suffers from certain drawbacks which are addressed by the development of the present invention. For example, the Wilson and Brecht devices both require extensive folding of a layered structure prior to compression, if any, of the tampon pledget. Additionally, neither device uses layers of rayon and cotton to achieve the benefits of the present invention. The Lewing and Donohue devices do not make the most effective use of a layered structure because layers of cotton are located on the outside of the uncompressed pledget, and because the presence of superabsorbent material is needed to achieve the benefits of those devices. Tampons constructed of homogenous blends of rayon and cotton do offer some improvements in fluid retention over those constructed of rayon alone, but the presence of cotton in the blend tends to erode the fluid acquisition rate benefit of the rayon.

A need, therefore, exists for an improved absorbent tampon comprising layers of rayon and cotton which optimizes the performance benefits of each of these materials. Specifically, such a tampon should demonstrate high fluid acquisition rate simultaneously with a high fluid retention capability. The tampon should be inexpensive and easy to manufacture and be constructed in such a manner as to offer performance improvements over blown tampons which employ rayon and cotton in their construction.

SUMMARY OF THE INVENTION

This invention relates to absorbent tampons, and more particularly an absorbent tampon comprising a layered structure constructed from layers of rayon and cotton.

The tampon pledget of the present invention is in the form of a laminar pad. The pledget comprises at least an uppermost layer, a lowermost layer, and at least one intermediate layer positioned between the uppermost layer and the lowermost layer. The uppermost layer and the lowermost layer are each comprised primarily of rayon. At least one intermediate layer is comprised primarily of cotton. In a particular aspect of the invention, the outer layers (i.e. the uppermost layer and the lowermost layer) are comprised of at least about 60% rayon, more preferably at least about 90% rayon, and even more preferably entirely of rayon. In another aspect of the invention at least one intermediate layer is comprised of at least about 60% cotton, more preferably at least 90% cotton, and even more preferably entirely of cotton.

The tampon pledget of the present invention may also incorporate a thin overwrap surrounding the discrete layers. This overwrap may preferably be comprised of rayon. In one aspect of the invention, the total number of layers is three (i.e. the uppermost layer, the lowermost layer, an one intermediate layer). Four total layers may also be used. The tampon pledget may be constructed of discrete layers. Alternatively, the uppermost and lowermost layers may be an integral layer which is wrapped around the intermediate layer or layers.

A tampon pledget according to the present invention may also be constructed as a laminar pad comprising an odd number of alternating layers of a first type and a second type. The layers of the first type comprise the outer layers (i.e. an uppermost layer and a lowermost layer) as well as alternating intermediate layers. The layer or layers of the second type comprise alternating intermediate layers. The layers of the first type comprise primarily rayon. The layers of the second type comprise primarily cotton. In one embodiment, the tampon pledget may have a total of five alternating layers.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

The present invention is directed to an absorbent tampon pledget comprising layers of rayon and cotton. The tampon pledget may be compressed to form an absorbent tampon, such as a tampon for menstrual use.

Figure 1:
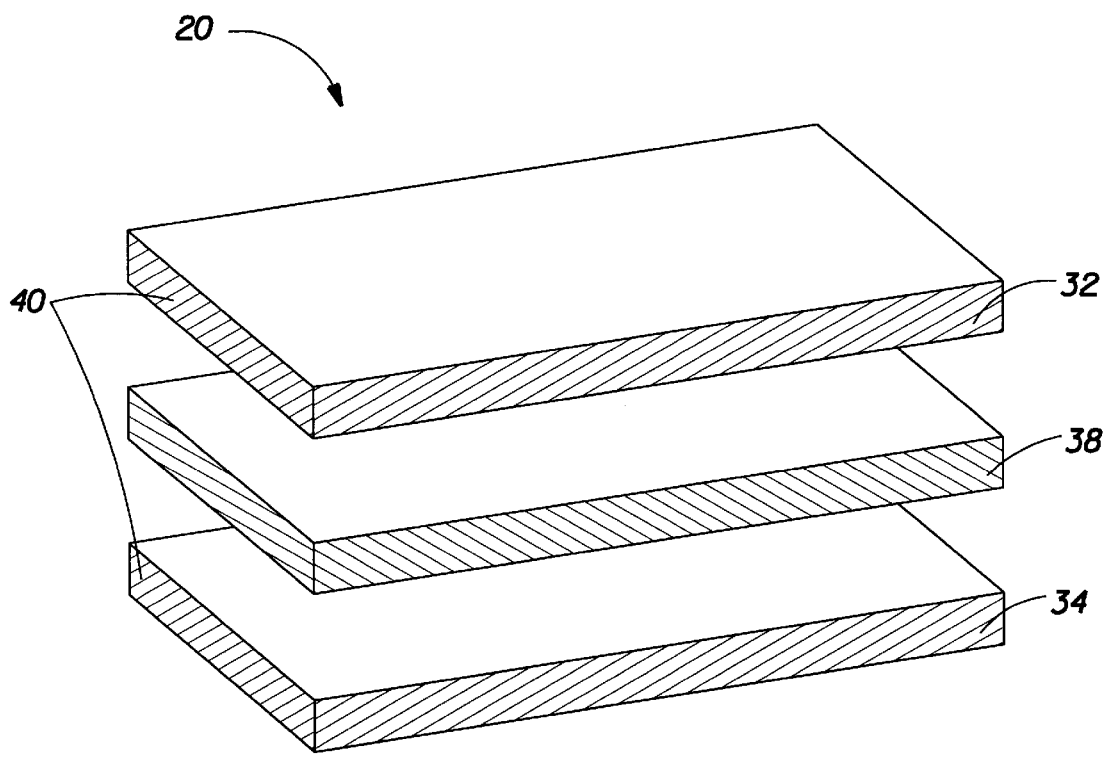
FIG. 1 is an exploded perspective view of a tampon pledget of the present invention.
Figure 2:
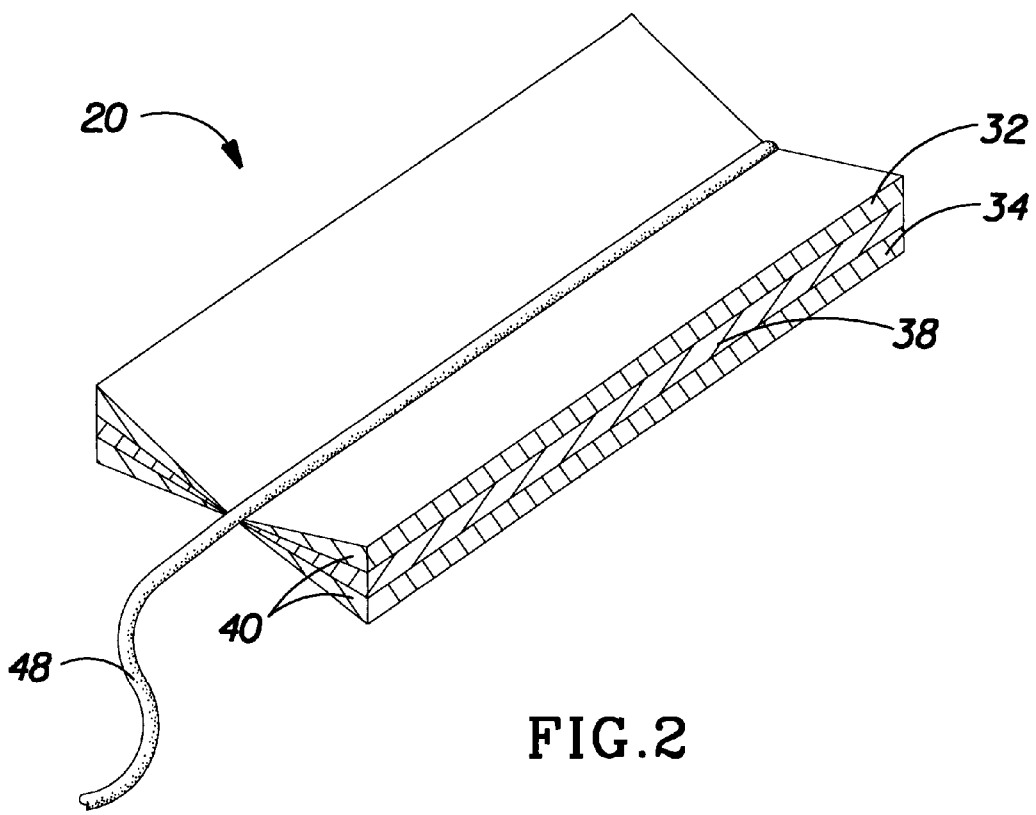
FIG. 2 is a perspective view of a tampon pledget of the present invention in its assembled configuration prior to compression to form a catamenial tampon.

FIGS. 1–2 show one embodiment of such an absorbent tampon pledget, tampon pledget 20. The present invention, however, is not limited to a structure having the particular configuration shown in the drawings.

As used herein the term "tampon" refers to any type of absorbent structure which is inserted into the vaginal canal or other body cavities for the absorption of fluid therefrom. Typically, tampons are constructed from an absorbent material which has been compressed in either the radial direction, the axial direction, or both in order to provide a tampon which is of a size and stability to allow insertion within the vagina or other body cavity. As used herein the terms "pledget" or "tampon pledget" are intended to be interchangeable and refer to a construction of absorbent material prior to the compression of such construction into a tampon as described above. Tampon pledgets are sometimes referred to as a tampon blanks, or a softwind, and the term "pledget" is intended to include such terms as well.

In one preferred embodiment of the present invention, the tampon pledget 20 is constructed in the manner shown in FIG. 1. The tampon pledget 20 shown on FIG. 1 is a generally, rectangular, flat, laminar pad. While the pledget shown in FIG. 1 is generally rectangular, other shapes such as trapezoidal, triangular, hemispherical, and chevron shaped are also acceptable. The pad is comprised of an uppermost layer 32 and a lowermost layer 34. Collectively, the uppermost layer 32 and the lowermost layer 34 are referred to as the outer layers 40. In addition to the outer layers 40, the tampon pledget 20 comprises at least one intermediate layer 38 positioned between the uppermost layer 32 and the lowermost layer 34.

In the embodiment shown in FIG. 1, each of the layers comprising the tampon pledget 20 is a discrete layer. The term "discrete layer" means a layer which is independent of the other layers comprising the tampon pledget 20. While a single layer folded over itself may be thought of as two layers, such a configuration is not two discrete layers as the term is used herein. The term "integral layers" means a layer which is constructed as a continuous web or patch and is folded upon itself either directly or with additional layers between the folds. Laminar pads of both constructions, that is pads constructed entirely of discrete layers and pads constructed of folded integral layers, are within the scope of the present invention. The tampon pledget 20 of the present invention comprises at the least the outer layers 40 and one or more intermediate layer 38. Each of the layers may be independent of all others, but need not be. While the layers may ultimately be folded prior to compression of the pledget 20, such folding is not necessary in all embodiments of the present invention.

The outer layers 40, that is the uppermost layer 32 and the lowermost layer 34, are each constructed primarily of rayon. Each of the outer layers 40 need not have an identical material composition, but each must be comprised primarily of rayon. Preferably, each of the outer layers 40 is comprised of at least about 60% rayon, more preferably at least about 90% rayon. In a particularly preferred embodiment, the uppermost layer 32 and the lowermost layer 34 are each constructed entirely of rayon. Constructing the outer layers 40 entirely from rayon, offers the benefits of ease of fabrication while retaining the benefits of inter-layer synergy.

At least one intermediate layer 38 is constructed primarily of cotton. Preferably such intermediate layer is at least about 60% cotton, more preferably at least about 90% cotton. In a particularly preferred embodiment, at least one intermediate layer 38 is comprised entirely of cotton.

The rayon used in the tampon pledget 20 of the present invention may be any suitable type typically used in disposable absorbent articles intended for in vivo use. Such acceptable types of rayon include GALAXY Rayon (a tri-lobed rayon structure) available as 6140 Rayon from Courtaulds Fibers Ltd., of Hollywall, England. SARILLE L rayon (a round fiber rayon), also available from Courtaulds Fibers Ltd. is also suitable. Any suitable cotton material may be used in the tampon pledget 20 of the present invention. Suitable cotton material includes, long fiber cotton, short fiber cotton, cotton linters, T-fiber cotton, card strips, and comber cotton. Preferably, the cotton layers should be a scoured & bleached cotton absorbent with a glycerin finish.

It has been found during development of the present invention that cotton and rayon each possess certain performance characteristics and properties. It has been further found that when rayon and cotton are combined in the layered arrangement described, the resulting tampon pledget demonstrates superior performance characteristics not achieved in previous tampon pledgets.

Rayon is a preferred material for use in tampons because of its high fluid absorption rate. Additionally, rayon is highly compressible and has a high fluid capacity on a gram per gram basis. One disadvantage with rayon, however, is that it tends to release previously absorbed fluid when subjected to an external confining pressure. This phenomenon, sometimes referred to as compression failure or "squeeze out," is discussed further in U.S. Pat. No. 3,749,094. The forces exerted on the tampon by the wearer's body movements or muscle contraction may lead to compression failure.

Cotton typically has a lower fluid acquisition rate than rayon and a lower absorbent capacity than rayon a gram per gram basis. Nevertheless, cotton is a preferred material for use in tampons because of its superior ability to retain acquired fluid when subjected to external confining pressures.

The absorption rate and total capacity of rayon decreases significantly when subjected to external confining pressures approximating those expected to be seen by a tampon during use. Similarly, cotton demonstrates a reduction in capacity when subjected to these forces, but the effect is less pronounced than is the case with rayon. Tampons constructed of homogenous blends of 50% rayon and 50% cotton do offer some improvements in fluid retention over those constructed of rayon alone, but the presence of cotton in the blend tends to erode the fluid acquisition rate benefit of the rayon. Significant improvements in the absorption rate of the tampon, and further reductions in squeeze out are achieved by the layered structure of the present invention, as compared to homogenous blends of rayon and cotton. The outer layers 40 of rayon act as a soft, highly compressible material which quickly absorbs fluid. This fluid is then transferred to the intermediate layer 38 comprised of cotton which is advantageous for long-term storage—particularly in the presence of pressure.

Figure 3:
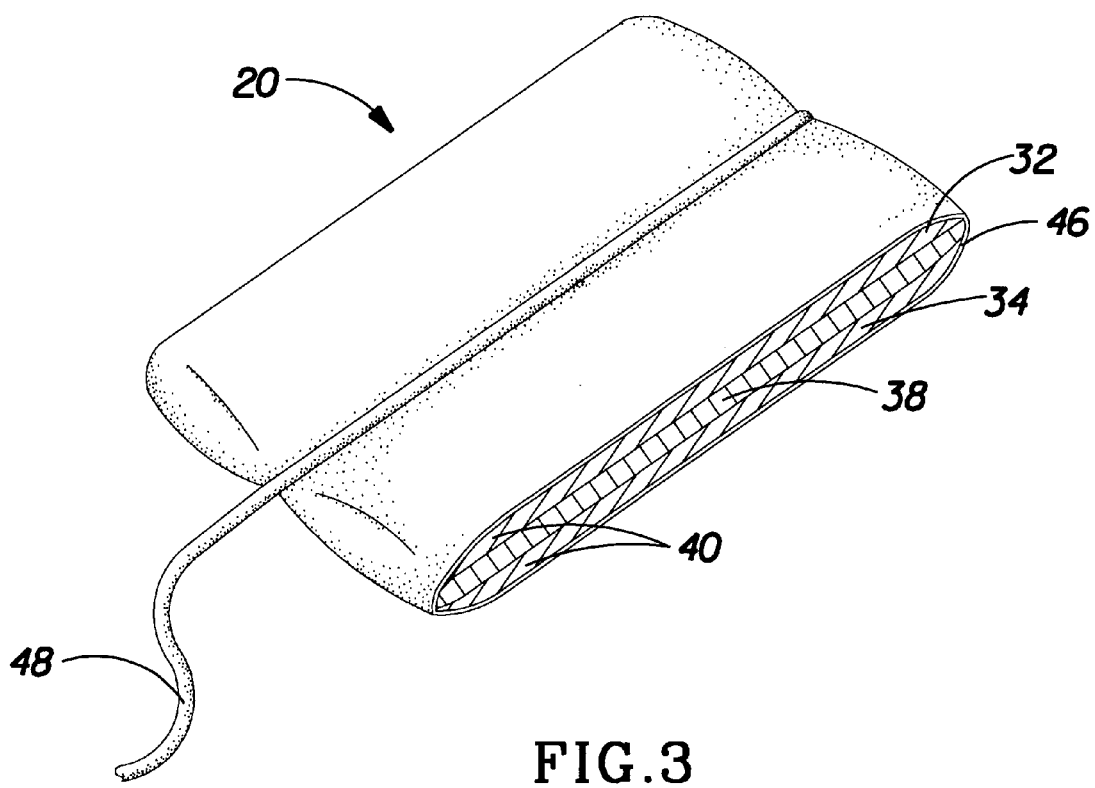
FIG. 3 is a perspective view of a tampon pledget of the present invention, which is similar to FIG. 2, but showing the addition of an optional overwrap.

The layered tampon pledget 20 is completed as shown in FIG. 2 with the above-described layers deposited on top of each other. Optionally, the layers may be wrapped with a relatively thin overwrap 46, as shown in FIG. 3. The overwrap 46 may be made of any suitable material and serves to help prevent surface fibers from the pledget 20 from coming loose in the wearer's body. A preferred material for the overwrap 46 is rayon, although other materials including bicomponent fibers, or other natural or synthetic fibers, may also be suitable. The overwrap 46 does not typically contribute significantly to the overall absorbency of the tampon pledget 20 and is therefore not considered one of the layers of the present invention. As shown in FIG. 3, the overwrap 46 may wrap the major surfaces and may also wrap the ends of the pledget 20 while leaving the sides uncovered. In one optional variation, the overwrap 46 may completely surround all surfaces of the pledget 20 including the sides. In another optional variation, the overwrap 46 may surround the sides and the major surfaces of the tampon pledget 20, but not cover the ends.

Each of absorbent layers of the tampon pledget 20 may have a basis weight of about 50 g/m$^2$ to about 250 g/m$^2$. The overwrap 46 layer may have a basis weight of about 10 g/m$^2$ to about 50 g/m$^2$.

Figure 4:
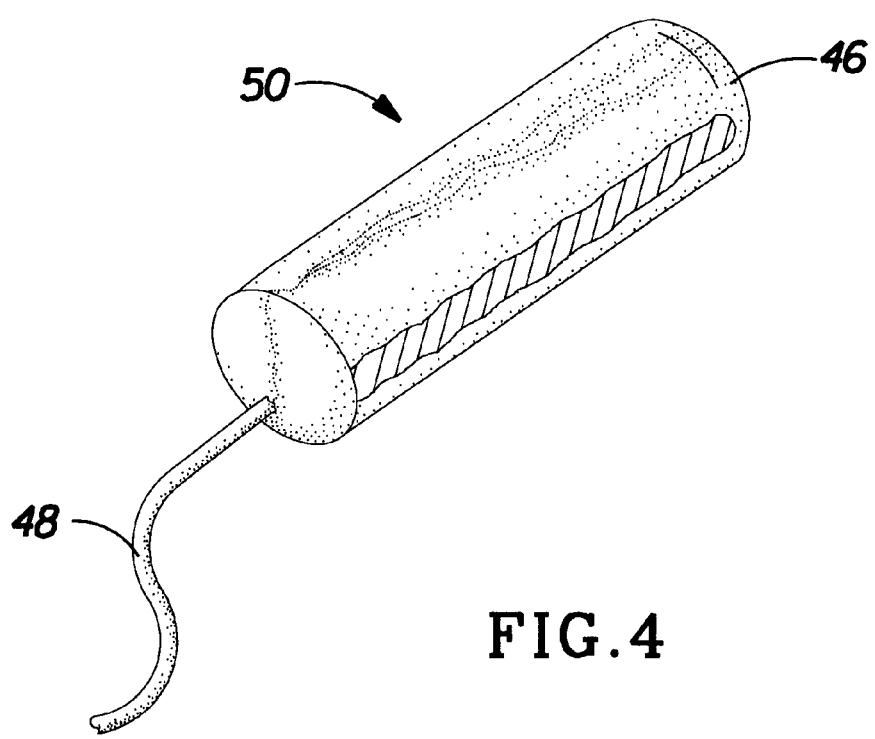
FIG. 4 is a catamenial tampon formed by compression of a tampon pledget of the present invention.

A withdrawal cord 48, an example of which is shown in FIG. 2, is typically attached to the pledget 20 for removal of the tampon after use. The withdrawal cord 48 may be attached in any suitable manner known in the art including sewing, adhesive attachment, or a combination of known bonding methods. To form a tampon ready for use, the tampon pledget 20 is compressed and heat conditioned in any suitable conventional manner. Pressures and temperatures suitable for this purpose are well known in the art. Typically, the pledget 20 is compressed in both the radial and axial direction using any means well known in the art. While a variety of techniques are known and acceptable for these purposes, a tampon compressor machine available from Hauni Machines, Richmond, Va., is suitable. FIG. 4 shows a completed tampon 50 according to the present invention after it has been compressed. As shown in FIG. 4 the bulk of the exposed surface of a tampon 50 constructed from a tampon pledget 20 of the present invention tends to comprise the thin overwrap 46 (when an overwrap is used). In the absence of an overwrap 46, the outermost layers 40 themselves will comprise the bulk of the surface area of the compressed tampon 50. Consequently, the benefits of the layering of the tampon pledget 20 of the present invention are realized even following compression of the pledget 20 into a completed tampon 50.

Advantages of the tampon pledget 20 of the present invention include its low cost, ease of construction, and employment of readily available and proven materials. The tampon pledget 20 need not have, and preferably does not have, any superabsorbent material incorporated therein. Each of the layers of the pledget 20 may be approximately the same thickness and provide all the necessary total absorbency for the finished tampon.

Figure 5:
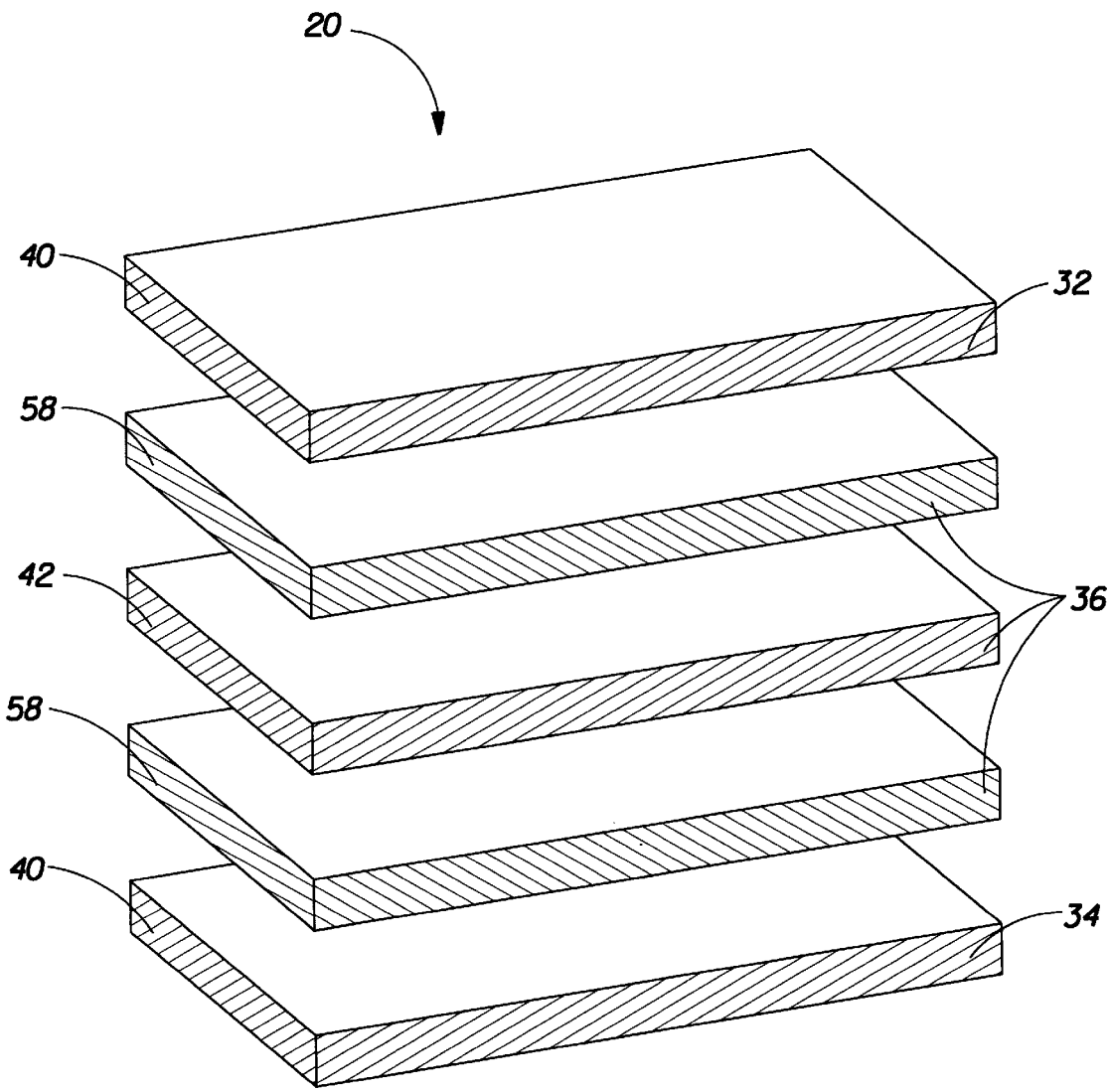
FIG. 5 is an alternate embodiment of a tampon pledget of the present invention showing a five layer structure.

Other variations on the embodiment of the present invention shown in FIGS. 1–2 are also possible. For example, a five layer structure, as shown in FIG. 5 may also be employed. In such an embodiment the outer layers 40 (i.e. the uppermost layer 32 and the lowermost layer 34) are comprised primarily of rayon. The layers positioned between the uppermost layer 32 and the lowermost layer 34 are collectively referred to as the interior layers 36. At least one of these interior layers 36 is comprised primarily of cotton. In the embodiment shown in FIG. 5, the tampon pledget 20 has alternating layers of rayon and cotton. There are, therefore, two cotton layers 58 located adjacent each of the outer layers 40. The central layer 42 may be a cotton layer, a rayon layer, or a blended layer. In the embodiment shown in FIG. 5, the central layer 42 is an additional rayon layer to preserve the alternating layer relationship and to better distribute fluid as the tampon becomes saturated.

Figure 6:
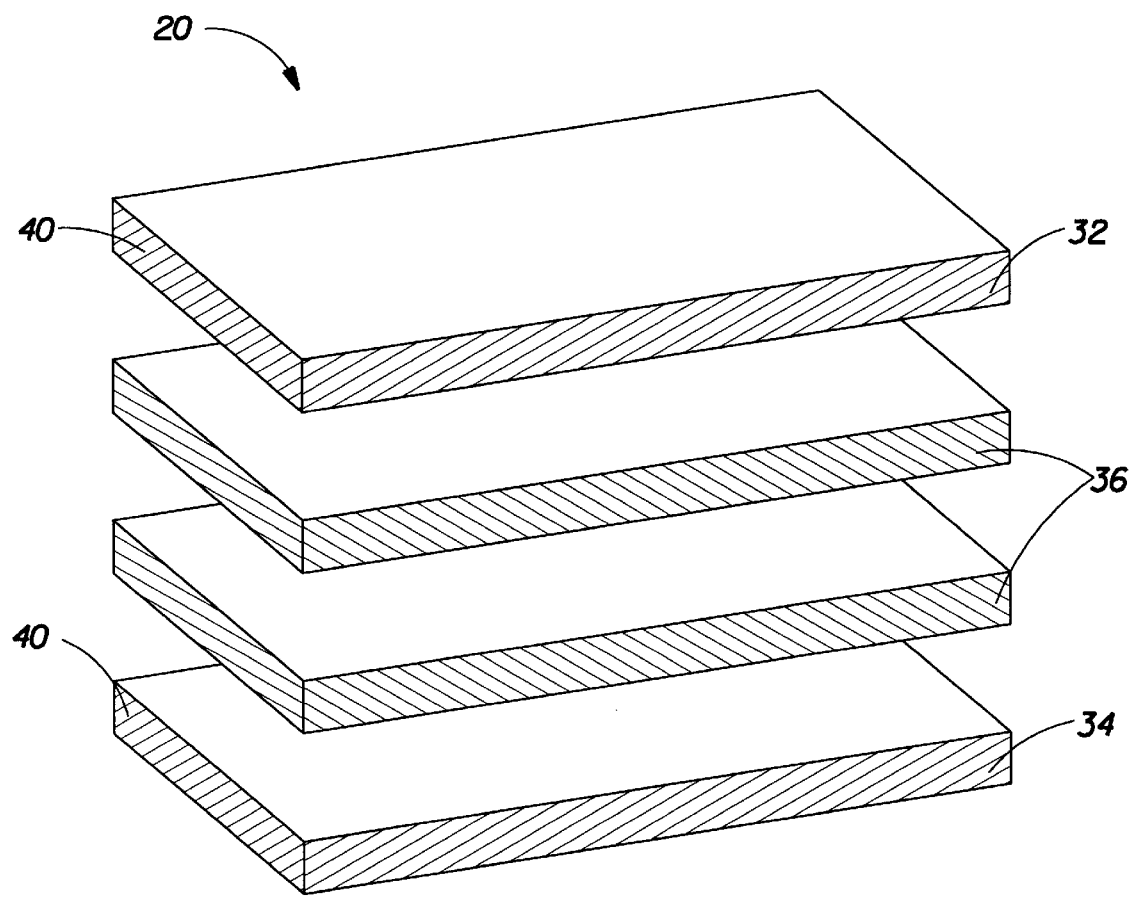
FIG. 6 is another alternate embodiment of a tampon pledget of the present invention showing a four layer structure.

Another embodiment of the tampon pledget 20 of the present invention is shown in FIG. 6. This embodiment is a four layer structure. The uppermost layer 32 and the lowermost layer 34 are comprised primarily of rayon in accordance with the present invention. At least one of the interior layers 36 is comprised primarily of cotton. In the embodiment shown in FIG. 6 both interior layers 36 are comprised of cotton.

Figure 7:
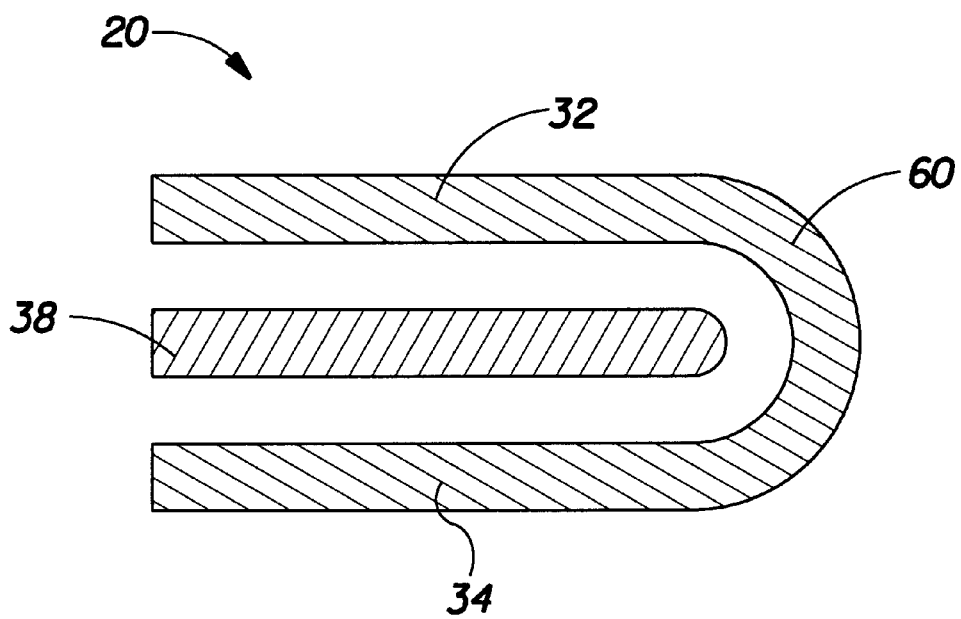
FIG. 7 is another alternate embodiment of a tampon pledget of the present invention showing an integral uppermost and lowermost layer wrapped around the intermediate layer.

Yet another embodiment of the tampon pledget 20 of the present invention is shown in FIG. 7. This embodiment uses an integral layer 60 comprised primarily of rayon, in accordance with the present invention, as both the uppermost layer 32 and lowermost layer 34. The integral layer 60 is wrapper around the intermediate layer 38. One intermediate layer 38 may be used, or a plurality of such layers may be used. At least one of such intermediate layers 38 is constructed primarily of cotton. The intermediate layer 38 or layers may be discrete or integral. One benefit using such an integral layer 60 as shown in FIG. 7 is the portion of the tampon pledget 20 which will become the head of the compressed tampon may also be comprised primarily of rayon. This allows the advantages described above for the layered structure to extend into the head of the tampon as well as the tampon body.

One variation on the embodiment shown in FIG. 7 might include a two layer initial structure. For example, an upper layer comprised primarily of rayon might overlay a lower layer comprised primarily of cotton. The two layers may then be folded as a unit such that the resulting uppermost layer and lowermost layer are comprised primarily of rayon. The primarily cotton layer in such a structure would then be the intermediate layer and be folded over on itself once.

Figure 8:
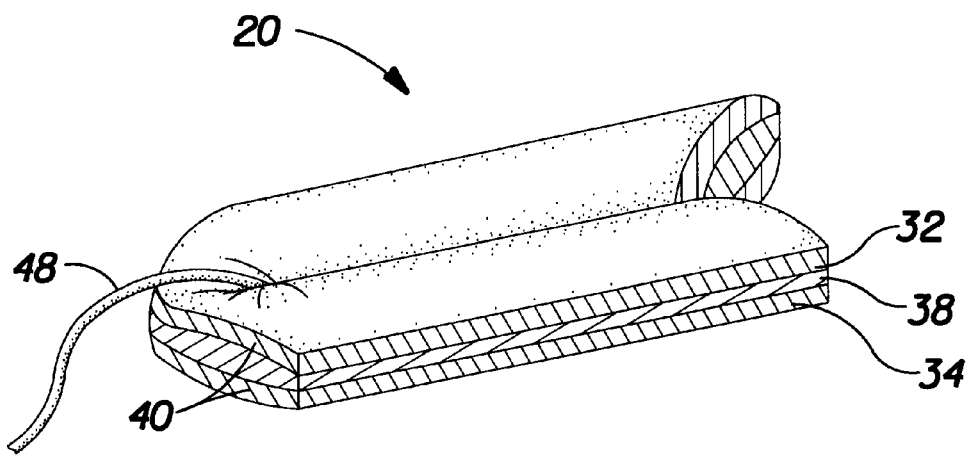
FIG. 8 is an embodiment of a tampon pledget of the present invention having a chevron shape.

FIG. 8 shows a variation on the shape of the tampon pledget 20 of the present invention. In the embodiment shown in FIG. 8 the tampon pledget 20 has a chevron shaped plan view prior to compression.

Other variations on the tampon pledget 20 of the present invention are also possible. Any total number of layers may be used. The layers need not overlap completely an d may be oriented in different directions. The arrangement and composition of the layers may vary providing the outer layers are comprised primarily of rayon and at least one intermediate layer is comprised primarily of cotton.

While particular embodiments of the present invention have been illustrated and described, it would be obvious to those skilled in the art that various other changes and modifications can be made without departing from the spirit and scope of the invention.

What is claimed is:

1. A tampon pledget in the form of a laminar pad, said tampon pledget comprising: an uppermost layer, a lowermost layer, at least one intermediate layer positioned between said uppermost layer and said lowermost layer, and an overwrap comprising rayon wherein the overwrap covers the tampon pledget, each of said uppermost layer and said lowermost layer is comprised entirely of rayon, and wherein said at least one intermediate layer is comprised entirely of long cotton fibers and without the presence of any superabsorbent material.

2. The tampon pledget of claim 1 wherein the total number of layers is three.

3. The tampon pledget of claim 1 wherein the total number of layers is four.

4. The tampon pledget of claim 1 wherein each of said uppermost layer and said lowermost layer is a discrete layer.

5. The tampon pledget of claim 1 wherein said uppermost layer and said lowermost layer are constructed from an integral layer which is wrapped around said at least one intermediate layer.

6. The tampon pledget of claim 1 wherein said pledget is generally rectangular in shape.

7. The tampon pledget of claim 1 wherein said pledget is chevron shaped.

8. A tampon pledget comprising a laminar of an odd number of alternating layers of a first type and a second type, wherein said layers of said first type comprise at least an uppermost layer and a lowermost layer, and an overwrap comprising rayon wherein the overwrap covers the tampon pledget, said layers of said first type being comprised entirely of rayon, said tampon pledget further comprising at least one layer of said second type, said at least one layer of said second type being comprised entirely of long cotton fibers and without the presence of any superabsorbent material.

9. The tampon pledget of claim 8 wherein the number of said alternating layers is five.

* * * * *